United States Patent [19]

Näslund

[11] Patent Number: 4,628,940
[45] Date of Patent: Dec. 16, 1986

[54] DEVICE FOR SAMPLING CELLS FROM THE MUCOUS MEMBRANE OF THE CERVIX UTERI

[76] Inventor: Jan I. Näslund, Vassvägen 21,, S-141 39 Huddinge, Sweden

[21] Appl. No.: 528,691

[22] Filed: Sep. 1, 1983

[30] Foreign Application Priority Data

Sep. 15, 1982 [SE] Sweden .................................. 8205272

[51] Int. Cl.⁴ ............................................. A61B 10/00
[52] U.S. Cl. ....................................... 128/750; 604/35
[58] Field of Search .................. 128/749, 750; 604/35, 604/43

[56] References Cited

U.S. PATENT DOCUMENTS

| | | | |
|---|---|---|---|
| 3,626,928 | 12/1971 | Barringer | 128/750 |
| 3,636,940 | 1/1972 | Gravlee | 128/750 |
| 3,735,751 | 5/1973 | Katz | 128/750 |
| 3,929,126 | 12/1975 | Corsaut | 604/43 |
| 4,190,059 | 2/1980 | Holt | 128/750 |

*Primary Examiner*—Edward M. Coven

[57] ABSTRACT

The sampling device includes means for spraying or flushing the mucous membrane with a liquid, in order to release cells therefrom, and a container for collecting the liquid together with cells suspended therein. The spray means of the device includes a rinsing or flushing pipe (3) having connected thereto a spray nozzle (4) which is connected to a liquid container, and a suction tube (5) for removing the liquid, together with the suspended cells, to the collecting container (19) by suction.

13 Claims, 5 Drawing Figures

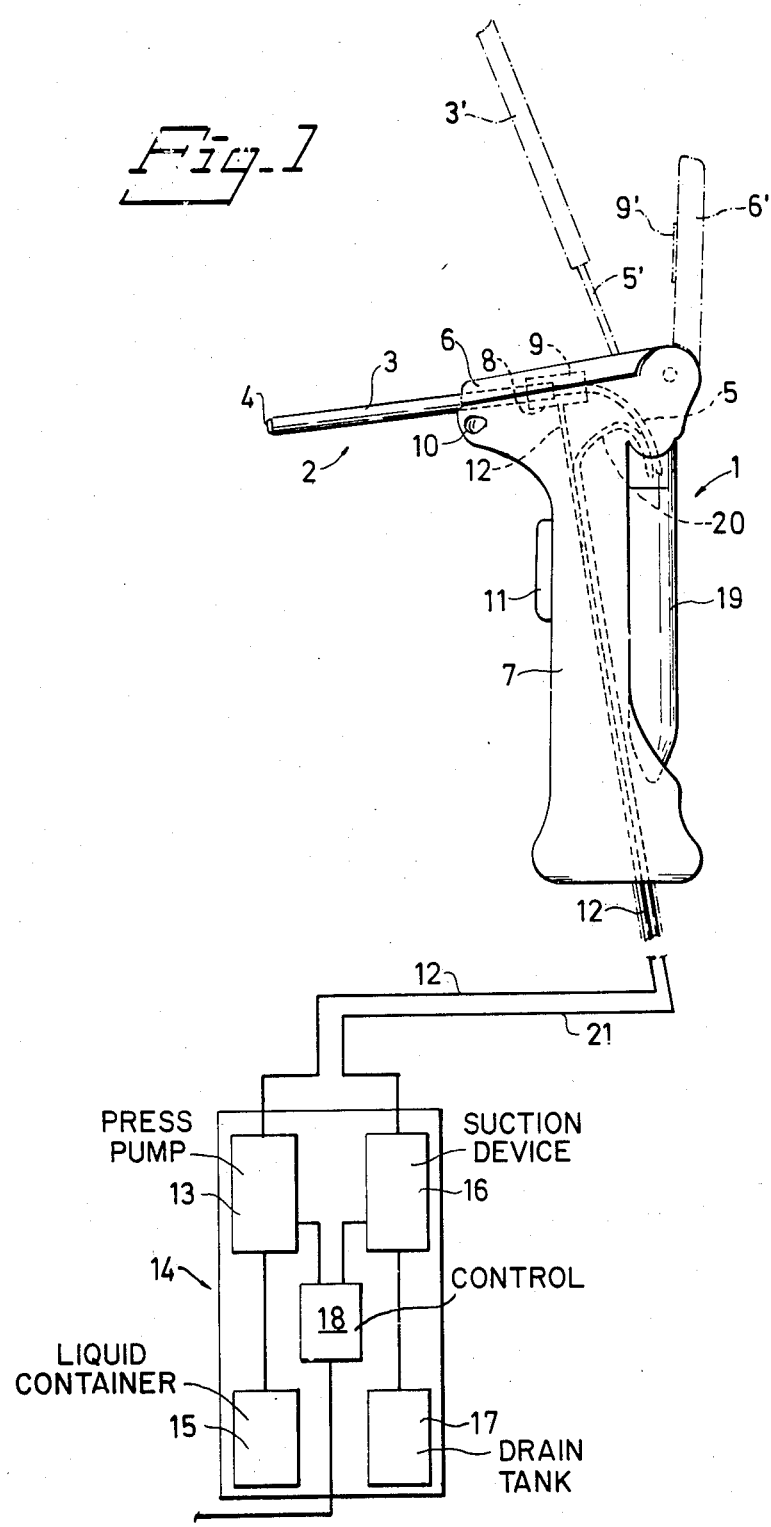

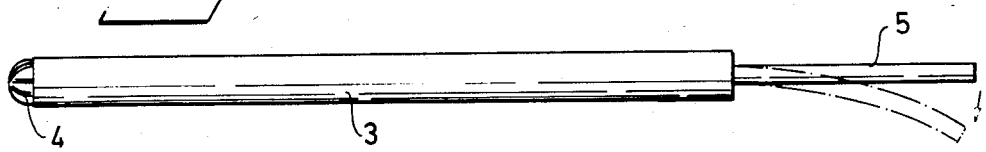
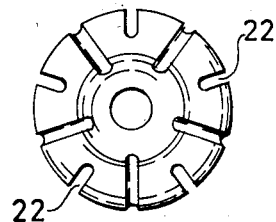
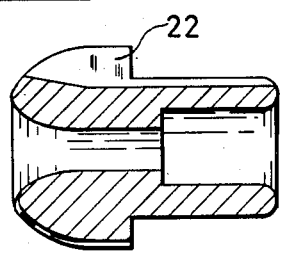
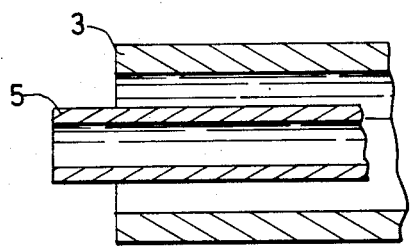

DEVICE FOR SAMPLING CELLS FROM THE MUCOUS MEMBRANE OF THE CERVIX UTERI

The present invention relates to a device for sampling cells from the mucous membrane of the cervix uteri, said device including means for spraying or flushing the mucous membrane with liquid so as to release cells therefrom, and a container for collecting the liquid with said cells suspended therein.

At present, cell samples are taken from the mucous membrane of the cervix uteri, by scraping the mucous membrane with a spatula. The sample thus removed is smeared onto a glass plate or slide and examined under a microscope. This method is emcumbered with a number of disadvantages. Thus, certain parts of the cervix uteri are difficult to reach, and even those surfaces which are readily accessible may exhibit cavities which cannot be reached with the spatula. Consequently, there is a risk that certain parts of the cervix uteri cannot be reached at all with the spatula, and consequently no cell samples will be taken from these surfaces. Moreover, a sample which has been taken by scraping with a spatula will contain secretion and mucous, which makes it difficult to examine the sample under a microscope. It is also difficult to transfer the whole of the sample onto the glass plate, and consequently only part of the sample is normally transferred successfully. Consequently, the sample ultimately examined under the microscope is often a non-representative selection of the cells present on the cervix uteri. The risk of error in the examination of a sample is therefore high, and the diagnosis made on the basis of the result of the examination will be incorrect. Because of the unreliability of sampling methods known hitherto, it is possible that, for example, cancer cells will go undetected. Needless to say, such an occurrence is most unsatisfactory.

An object of the present invention is to provide a device by means of which the aforementioned disadvantages relating to the sampling of cells from the mucous membrane of the cervix uteri can be overcome.

The device according to the invention is characterized in that the spraying means includes a rinsing or flushing pipe having connected thereto a spray nozzle, which is connected to a liquid container, and further includes a suction pipe for removing the liquid, with the cells suspended therein, to the collecting container by suction.

The invention will now be described in detail with reference to the accompanying drawins, in which FIG. 1 is a schematic side view of an embodiment of the device according to the invention, FIG. 2 is a side view of the detachable spraying unit of the device illustrated in FIG. 1, FIG. 3 is an enlarged front view of the nozzle of the spraying unit according to FIG. 2, FIG. 4 is an axial section of the nozzle illustrated in FIG. 3 and FIG. 5 is an enlarged axial section view of the end part of the flushing pipe and the suction tube of the spraying unit illustrated in FIG. 2. Corresponding parts are designated by the same reference numerals in the different Figures.

The device illustrated in the drawing has the form of a spray gun having a handgrip 1 in which all sampling functions are incorporated, and a spraying means 2 which comprises a rinsing or flushing pipe 3, having a spray nozzle 4, and a suction tube 5 coaxial with pipe 3. The upper part 6 of the handgrip is pivotally connected to the lower part 7 of said handgrip. The flushing or rinsing pipe 3, the nozzle 4 and the suction tube 5 together form a unit which is detachably connected to the handgrip and which is replaced after each patient examined. This unit is connected to the handgrip via a sealing 8, which holds said unit by means of a second sealing 9. The lower part 7 of the handgrip also houses a light source 10. The lower part 7 of the handgrip is provided with a press button 11, which is intended for providing a regulatable rinsing pressure in the rinsing or flushing pipe 3. The rinsing or flushing pipe 3 is connected, via a pressure hose 12, to a high-pressure pump 13, which is incorporated in a unit 14 and connected to a rinsing-liquid container 15. The unit 14 also includes a suction device 16, a drain tank 17 connected to said suction device, and electronic control means 18, and said unit may be located at a selected distance from the place at which sampling takes place, and hidden from view. The suction tube 5 is connected to the collecting container 19, which comprises a sediment tube or centrifugal tube. The container 19 is detachably connected to the hand grip 1. The container 19 is also provided with a suction pipe 20 functioning as a weir means, which is connected to the suction means 16, via a suction hose 21.

The spray nozzle 4 is provided with gracile rinsing ducts 22, for example five in number, which have a dimension of 0.25 mm×0.25 mm, and which prevent large quantities of liquid from flowing out, but which nevertheless permit a high kinetic energy to be obtained in respect of the liquid jets, due to the high pressure of the liquid, which is a necessary condition for successful loosening of cells from the mucous membrane by rinsing. The jets must have a high velocity and must not emerge from one single aperture as a diverging jet stream would imply that the effect would be very strong near the nozzle but much weaker a little distance away from the nozzle. By means of the gracile ducts 22 according to the invention such problems are avoided. Different effects can be obtained by using the device according to the invention at known working pressures. During the initial stages of the sampling procedure there is used a low rinsing pressure (about 1 bar), this low pressure being provided by pressing the button 11 to a low pressure position. In this way, purulent liquidities can be removed from the cervix uteri, and liquid containing such purulent liquidities runs to a drain tank. In order to release cells from the mucous membrane of the cervix uteri a high pressure is required (5-5 bar), which can be produced by pressing the button 11 to a high pressure position. The effect of the jet will be high thanks to the high velocity of the water molecules. The area effectively sprayed will be many times larger than the area of the jet and all cavities will be effectively sampled. This will cause liquid together with the collected cells to flow, via the suction tube 5 to the container 19. When the level of liquid in the container 19 reaches the level of the suction pipe 20, all further liquid will run into the suction device 16, and from there to the drain tank 17. The amount of cell-containing liquid in the container 19 will constantly reach a standardized level, which means that neither the container nor the centrifugal tube 19 need be weighed when arriving at the laboratory. All tubes from the various different apparatuses will be equally filled.

Since all sampling functions are incorporated in the handgrip 1, it is possible to operate the handgrip with one hand. The high pressure pump 13 may have a size such as to provide about 60–100 ml liquid per minute, and may have a maximum pressure of about 15 bar. The suction device 16 may comprise a membrane suction means. The tanks 15 and 17 may have a volumetric capacity of 1-2 liters.

The position of the detachable unit 3, 4, 5 in which it is mounted into the handgrip is designated by 3', 4', 5'. The upper part 6 of the handgrip is pivotable to position 6' when mounting said unit into the handgrip.

I claim:

1. A device for obtaining cell samples from the mucous membrane of the cervix uteri for the detection of cervical cancer comprising:
   spray nozzle means (4) for applying, to the cervical mucous membrane, a plurality of liquid jets positively pressurized at a pressure between 5 and 15 bar to have sufficiently high kinetic energy to dislodge a diagnostically adequate sample of cells from the mucous membrane by the impact of the liquid on the mucous membrane;
   a liquid supply pipe (3) connected to said spray nozzle means and connectable to a source of pressurized liquid;
   a suction tube (5) opening adjacent said spray nozzle means for removing the liquid and dislodged cells; and
   a collecting container (19) coupled to said suction tube for receiving the liquid and cells from said tube.

2. The device according to claim 1 further including a handgrip (1) for holding the device and wherein said spray nozzle means, liquid supply pipe, and suction tube are integrally formed as a unit detachably connectable to said handgrip.

3. The device according to claim 1 further including a handgrip (1) for holding of the device and wherein said collecting container (19) is detachably connectable to said handgrip.

4. The device according to claim 1 wherein said collecting container (19) is provided with a level controlling suction pipe (20) connectable to a suction source.

5. The device according to claim 1 further including means (11) coupled to said liquid supply pipe for controlling the pressure of the liquid between a low pressure at which the liquid cleanses the cervix uteri and a high pressure at which the liquid jets dislodge cells from the mucous membrane.

6. The device according to claim 1 wherein said spray nozzle means (4) is detachably connected to said liquid supply pipe (3).

7. The device according to claim 1 wherein said suction tube (5) is coaxial with said liquid supply pipe (3) and axially displaceable within it.

8. The device according to claim 1 wherein said spray nozzle means includes a plurality of circumferentially spaced ducts (22) communicating with said liquid supply pipe (3).

9. The device according to claim 8 wherein said spray nozzle means (4) includes a centrally located opening communicating with said suction tube (5).

10. The device according to claim 9 further including a recess coaxial with said central opening for receiving said suction tube (5).

11. The device according to claim 1 further including a positive pressure pump (13) and liquid supply container (15) couplable to said liquid supply pipe.

12. The device according to claim 1 further including a suction device (16) and drain tank (17) couplable to said collecting container.

13. The device according to claim 12 further including a level controlling suction pipe (20) opening into said container and couplable to said suction device and drain tank.

* * * * *

UNITED STATES PATENT AND TRADEMARK OFFICE
CERTIFICATE OF CORRECTION

PATENT NO. : 4,628,940

DATED : December 16, 1986

INVENTOR(S) : JAN I. NASLUND

It is certified that error appears in the above-identified patent and that said Letters Patent is hereby corrected as shown below:

In Column 2, line 49, delete "(5-5 bar)" and insert --(5-15 bar)--.

Signed and Sealed this

Twenty-fourth Day of March, 1987

*Attest:*

DONALD J. QUIGG

*Attesting Officer*  *Commissioner of Patents and Trademarks*